United States Patent [19]

Linn et al.

[11] Patent Number: 4,591,499
[45] Date of Patent: May 27, 1986

[54] METHOD FOR TREATMENT AND PREVENTION OF MASTITIS

[75] Inventors: Leighton L. Linn, Andrew County, Mo.; Robert J. Mathiesen, Douglas County, Nebr.

[73] Assignee: J. B. Lima, Inc., St. Joseph, Mo.

[21] Appl. No.: 572,707

[22] Filed: Jan. 20, 1984

[51] Int. Cl.$^4$ .................. A61K 39/00; A61K 37/00; A61K 39/02
[52] U.S. Cl. ........................ 424/93; 424/85; 424/88; 424/92; 426/2
[58] Field of Search ............... 424/88, 92, 93; 426/2, 426/13, 60, 61, 805, 807; 435/853–857

[56] References Cited

U.S. PATENT DOCUMENTS 1,758,937  12/1925  Earp-Thomas ............... 435/853
4,395,394  7/1983  Wolff et al. ................ 424/88

OTHER PUBLICATIONS

Amster et al, *Chem. Abst.*, vol. 93, No. 112484n, 1980, "Antibacterial Activity of Skim Milks Fermented with Lactic Bacteria".

*Primary Examiner*—Thomas G. Wiseman
*Assistant Examiner*—Robin Lyn Teskin
*Attorney, Agent, or Firm*—Kokjer, Kircher, Bradley, Wharton, Bowman & Johnson

[57] ABSTRACT

A method for treating mastitis in ruminants by the administration of non-pathogenic Lactobacilli. The Lactobacilli are preferably administered in an oil emulsion which includes a water and an oil soluble emulsifier.

25 Claims, No Drawings

METHOD FOR TREATMENT AND PREVENTION OF MASTITIS

BACKGROUND AND SUMMARY

This invention relates generally to mastitis treatment and prevention in mammals and, more particularly, to a method and composition of a non-antibiotic nature.

Mastitis has long been recognized as a complex disease of major economic significance to the dairy industry. While the disease is of primary concern to the dairy cow industry in the United States, it is also a considerable problem among goat herds and other commercial milk producing mammals. The disease is less prevalent but by no means unknown among swine and other species.

Mastitis may be defined as any inflammation of the mammary gland due to the effects of infection of the gland by bacterial or mycotic pathogens. Various factors can contribute to the onset of the infection including trauma, unsanitary conditions and direct or indirect contact with infected animals. With modern automatic milking equipment, if careful procedures are not followed, the risk of precipitating and spreading mastitis is great. The disease is, of course, not limited to animals being milked for human consumption but is encountered by nursing mothers in all species.

The best control for mastitis is optimum managerial practices with regard to milking, if applicable, and general herd management. Even with the best management practices, however, the disease cannot be completely eradicated and heretofore has been controlled only through the use of antibiotics. As these drugs have been widely used for a number of years, the pathogens have built resistance to them creating an automatic need for increasing dosages of existing antibiotics, and requiring the development of still further antibiotics to combat the more resistant strains.

The present invention addresses the problem of treating and preventing mastitis by changing conditions within the mammary gland so that the pathogens are unable to continue to exist and reproduce. Specifically, the present invention provides for introduction into the mammary gland of a quantity of useful bacteria which will produce sufficient lactic acid to lower the pH of the milk within the gland thus changing the environment so that the pathogens can no longer reproduce. The lactic acid production creates the isoelectric point of casein which causes the casein to precipitate. The pathogens will be trapped within the precipitate which serves as a vehicle for their removal. The gland is milked by hand to accomplish this.

OBJECTS OF THE INVENTION

The primary object of this invention is to provide a non-antibiotic method for treatment and prevention of mastitis.

As a corollary to the foregoing object, an important aim of the invention is to provide a treatment and prevention which is safe, non-toxic and has no known side effects.

A very important objective of this invention is to provide a method for the treatment and prevention of mastitis which will not stimulate the disease causing pathogens to produce strains which are resilient to the treatment composition.

As a corollary to the foregoing objective, an aim of the invention is to provide a treatment and prevention which eliminates conditions within the mammary gland which are favorable to reproduction of the pathogens rather than attacking and killing the pathogens directly.

Our invention has as an objective a method for the treatment and prevention of mastitis which is applicable to any mammal but is especially adapted for use with those mammals characterized by udders.

Other objects of the invention will be made clear or become apparent from the following description and claims.

DETAILED DESCRIPTION OF THE PREFERRED EMBODIMENT

Cultures of lactic acid producing bacteria have long been used in the manufacture of cheese, yogurt, buttermilk and other dairy products. Beneficial lactic acid producing bacteria have also been used in recent years as feed additives to promote better feed utilization in many types of animals.

In broadest form, the present invention encompasses a method for treating and preventing mastitis in mammals utilizing a composition comprising an oil emulsion of beneficial lactic acid producing bacteria. The quantity of viable bacteria present should be effective to lower the pH of the milk in the gland to at least about 5.0 to 6.5. Generally, a live bacteria count of at least $1 \times 10^3$ Colony Forming Units (CFU) should be present for each cubic centimeter (cc) of the oil emulsion. A preferred bacteria count is $1 \times 10^6$ CFU per cc of emulsion. While there is no upper limit on the bacteria count, since the bacteria utilized are non-toxic, a practical upper limit is $1 \times 10^9$ CFU per cc of emulsion.

There are various known strains of non-pathogenic lactic acid producing bacteria including some species of the genus Streptococcus and the entire genus Lactobacillus. Among the lactic acid producing species within these two generic categories are *Streptococcus lactus, Streptococcus cremoris, Streptococcus diacetylactis, Streptococcus thermophillus* and *Streptococcus faecium*. Also *Lactobacillus acidophilius, Lactobacillus alimentarius, Lactobacillus bifidus, Lactobacillus brevis, Lactobacillus buchneri, Lactobacillus bulgaricus, Lactobacillus casei, Lactobacillus catenaforme, Lactobacillus cellobiosus, Lactobacillus collinoides, Lactobacillus confusus, Lactobacillus curvatus, Lactobacillus delbrueckii, Lactobacillus farciminis, Lactobacillus fermentatae, Lactobacillus fermentum, Lactobacillus fructivorans, Lactobacillus fructosus, Lactobacillus helveticus, Lactobacillus heterohiochi, Lactobacillus hilgardii, Llactobacillus homohiochi, Lactobacillus jensenii, Lactobacillus lactis, Lactobacillus leichmannii, Lactobacillus malefermentans, Lactobacillus mali, Lactobacillus maltaromicus, Lactobacillus minutus, Lactobacillus pentoaceticus, Lactobacillus plantarum, Lactobacillus rogosae, Lactobacillus ruminis, Lactobacillus sake, Lactobacillus lalivarius, Lactobacillus sanfrancisco, Lactobacillus thermophilus, Lactobacillus trichodes, Lactobacillus viridescens, Lactobacillus vitulinus,* and *Lactobacillus xylosus.*

There are, of course, a number of known sub-species of the foregoing species, which sub-species can also be utilized. Those bacteria from the genus Lactobacillus are generally preferred for use in the present invention and, specifically, *Lactobacillus acidophilus,* and *Lactobacillus casei*. A combination of *Lactobacillus acidophilus* and *Lactobacillus casei* has been found to be particularly advantageous.

An oil emulsion of the live bacteria is the preferred medium for transportation and storage since it precludes the presence of water and oxygen which will allow reproduction of the bacteria. Any oil that is GRAS categorized (Generally Recognized As Safe) by the U.S. Food and Drug Administration is acceptable and this includes the broad category of unsaturated vegetable oils. Included in this group are corn oil, almond oil, castor oil, coconut oil, cottonseed oil, linseed oil, olive oil, palm oil, peanut oil, persic oil, sunseed oil, soybean oil and sesame oil. Largely for economic reasons, corn oil is the preferred emulsion vehicle at the present time.

Since the lactic acid producing bacteria are grown in an aqueous medium, both water soluble and oil soluble emulsifiers are utilized in forming the oil emulsion. The emulsifiers should have a hydrophylic-lipophylic balance (HLB) once admixed of about 3 to 15. An HLB for the water soluble emulsifier of about 13 to 16 and an HLB of about 3 to 5 for the oil soluble emulsifier will be sufficient.

Any GRAS categorized emulsifying agents meeting the foregoing criteria are acceptable for purposes of the present invention. This includes the mono and diglycerides of fat forming fatty acids which generally perform well as oil soluble emulsifiers and have relatively low HLB numbers. A preferred emulsifier is ATMOS 300, a combination of mono and diglycerides, which is a product of Kraft, Inc. of Memphis, Tenn.

Among the water soluble emulsifiers which can be utilized are polyoxyethylene sorbitan fatty acid esters. A particularly useful compound in the foregoing category is TWEEN 80, a product of ICI Americas Inc., Wilmington, Del. The emulsifiers should be used in a quantity of about 0.5% to 20% by volume of the oil, for each of the emulsifiers. A preferred composition will have 5.0% by volume of each of the emulsifying agents.

It is also desirable to include in the composition a suspension agent which will facilitate suspension of the bacteria in the oil emulsion. This is particularly desirable where plastic containers are utilized since the electrostatic charge on these tend to attract the bacteria to the walls of the container. Propylene glycol is a preferred suspension agent, although other suitable compounds include glycerin, polyethylene glycol, and sorbitol. The suspension agent should be present in a range of 0.5% to 20% by volume, preferably about 1.0% by volume.

To enhance the shelf life of the composition, an antioxidant such as vitamins C or E, or a substance containing one of these, may be utilized. For example, wheat germ oil, mixed tocopherole concentrate, d-alpha tocopherole acetate, and d-alpha tocopherole propionate may be added to the composition in a quantity of 1 to 100 International Units (I.U.) per cc of the oil emulsion. A preferable quantity is 10 I.U. per cc. It should also be recognized that the invention contemplates inclusion of other useful components such as vitamins, minerals and recognized healing agents in the composition of the invention, so long as the additives have no deleterious effect on the useful lactic acid producing bacteria.

In carrying out the method of the present invention, an effective quantity of one or more of the lactic acid producing bacteria is injected into the mammary gland and allowed to remain there until the milk in the gland is clabbered. By "effective quantity" is meant a sufficient number of CFU to produce sufficient lactic acid to lower the pH in the gland to where the pathogens can no longer reproduce and remain viable. This will generally be a pH below 7.0 and preferably about 5.0 to 6.5 or below. Clabbered milk is then removed, preferably by hand milking. Although not necessary in every case, in most cases the foregoing steps are repeated a second time on an 8-12 hour rotation. Additional repetition may be required in exceptional cases. With bovines and other udder characterized mammals, the teat canal provides a ready means of injection into the gland utilizing techniques well known to those skilled in treating mastitis with antibiotics. A quantity of the oil emulsion as heretofore described of about 6 to 15 ccs is adequate for most animals.

The exact mechanism by which the microorganisms in the composition utilized in the method of the present invention control mastitis is not entirely understood. It is known, however, that the pH of an infected gland will range from approximately 7.2 to 8.0. A healthy uninfected gland will have a pH of about 6.4 to 6.8. It is believed that the lactic acid producing bacteria cause the pH to drop sufficiently so that the pathogens can no longer reproduce as the environment approaches acidic conditions. Also, the lactic acid reacts with the milk itself to produce the isoelectric point of casein which will cause the casein to clabber thus entrapping the pathogens that are present and serve as a vehicle to remove these when the animal is milked after approximately 12 hours. Some of the useful bacteria will remain in the mammary gland even after the contaminated milk is removed thus continuing to provide protection for the animal by helping to control the pH in the gland. The combination of *Lactobacillus acidophilus* and *Lactobacillus casei* is particularly useful in carrying out the present invention since both of these non-pathogenic lactic acid producing bacteria will grow over a relatively wide pH range. Also, both of these species are found naturally in bovine milk and are therefore clearly compatible with the milk. *Lactobacillus casei* will continue to grow at relatively low temperatures which is another advantage to using this specie. *Lactobacillus acidophilus* has been found to be particularly susceptible to partially remaining in the udder after the pathogens are milked out thus enhancing the residual effect discussed above.

It has been found that the composition of the invention may be stored at room temperatures and will remain stable and viable for a period of several months. The following data is indicative of the efficacy of the composition and method herein claimed. While this data is for bovines, the similarity in etiology of infectious mastitis in cattle and other mammals, especially other mammals characterized by udders, is well known.

Three (3) milk cows each manifesting external indication of udder infection were treated as follows. Milk from a quarter that showed a high somatic cell count or swelling was cultured to determine the type of pathogen that was causing the infection. The quarter was then treated with 10 cc of a corn oil emulsion of *Lactobacillus acidophilus* and *Lactobacillus casei* in a 50—50 mixture. The CFU count of the bacteria was approximately $1 \times 10^6$ per cc of oil. 5% by volume of Tween 80 and 5% by volume Atmos 300 were used as emulsifying agents. One percent (1%) by volume propylene glycol and 10 I.U. of vitamin E per cc were also present. The emulsion was injected through the test canal. The treated quarters were milked by hand every 12 hours and reinfused using the foregoing preparation. The results are summarized below.

TABLE 1

| Animal | Infection Location | Pathogen Identified | 72 Hours From Treatment Onset |
|---|---|---|---|
| 1 | all quarters | hemo *staph aureus* enterobacter | no pathogens present |
| 2 | RR, LR | hemo *staph aureus* abundt bacillus sp | no pathogens present |
| 3 | RF, LF | abundt double zone hemo *staph aureus* | no pathogens present |

RR = right rear
RF = right front
LR = left rear
LF = left front

The following table indicates the effectiveness of various antibiotics relative to the pathogens identified above in the infected bovines. The following determinations were made utilizing the Kirby-Bauer Susceptibility Test, well known to those skilled in the art.

SUSCEPTIBILITY OF PATHOGENS TO ANTIBIOTIC TREATMENT

| Antibiotic | Hemo *Staph Aureus* | Weak Hemo *Staph Aureus* | Enterobacter |
|---|---|---|---|
| Ampicillin | − | − | |
| Cephalothin | + | − | |
| Chloramphenicol (Chloromycetin) | + | + | + |
| Erythromycin | + | − | − |
| Furazolidone (Furoxone) | + | + | + |
| Gentamicin | + | + | + |
| Kanamycin | + | | + |
| Lincomysin | | | |
| Methicillin | + | − | |
| Nitrofurazone (Furacin) | + | + | + |
| Novobiocin | + | − | − |
| Penicillin | + | − | |
| Vetisulid | + | | + |
| Streptomycin | − | | |
| Tetracycline | | + | + |
| Triple Sulfa | | + | − |
| Trimethoprim/ sulfamethoxazole | + | | + |
| Bacitracin | − | − | |

+ = sensitive
− = resistant

As indicated, the particular pathogens found in the infected animals are resistant to many of the available antibiotics which would not, therefore, be effective in treatment. The composition and method of the present invention, however, was 100% successful.

A second test encompassing 15 cows, all manifesting external indications of udder infection was conducted as follows. First, samples were taken from the infected quarters and bacterial isolates and somatic cell counts (SCC) taken. The teat was then sanitized and injected with 10 cc of a propylene glycol emulsion of *Lactobacillus acidophilus* and *Lactobacillus casei* in a 50—50 mixture. Other components were the same as set forth in the first test reported above. All cows received a second infusion twelve hours after the first. A second sample was taken one week later and again tested for somatic cell count and specific bacteria present. The results are summarized in Table 2.

TABLE 2

| Cow | Bacteria | SCC | Bacteria | SCC |
|---|---|---|---|---|
| 1 | α-strep | 21,757,000 | α-strep | 22,575,000 |
| 2 | NSI | 3,615,000 | NSI | 13,778,000 |
| 3 | E. coli | 14,424,000 | E. coli | 8,150,000 |
| 4 | Klebsiella | 4,126,000 | NSI | 6,003,000 |
| 5 | NSI | 5,716,000 | NSI | 852,000 |
| 6 | NSI | 3,515,000 | NSI | 1,493,000 |
| 7 | NSI | 12,821,000 | S. Aureus | 16,554,000 |
| 8 | NSI | 1,305,000 | NSI | 3,053,000 |
| 9 | NSI | 15,323,000 | NSI | 2,701,000 |
| 10 | E. coli | 13,867,000 | NSI | 2,113,000 |
| 11 | E. coli | 24,934,000 | NSI | 4,771,000 |
| 12 | NSI | 25,074,000 | α-strep | 22,027,000 |
| 13 | NSI | 25,264,000 | NSI | 819,000 |
| 14 | α-strep | 20,007,000 | α-strep | 5,677,000 |
| 15 | α-strep | 19,896,000 | NSI | 1,233,000 |

NSI — negative for Streptococcus infection
SCC — somatic cell count

As indicated, 10 of the fifteen cows tested in this group showed significant reduction in somatic cell count. A like number of control cows receiving no treatment did not show any reduction in SCC.

The foregoing data is only indicative of the results that have been observed with considerably larger numbers of animals. Accordingly, the invention has been found to meet all of the aims and objectives heretofore set forth.

We claim:

1. A method of controlling mastitis in mammals, said method comprising:
   introducing into the mammary gland of said mammals a non-toxic amount of one or more non-pathogenic lactic-acid producing live bacteria wherein said amount is sufficient to control mastitis;
   allowing said bacteria to remain in said gland in a viable state until milk present in the gland is clabbered; and
   removing the clabbered milk from said gland.

2. A method as set forth in claim 1, wherein said quantity of bacteria is sufficient to lower the pH of the gland to at least about 5.0 to 6.5.

3. A method as set forth in claim 1, wherein said bacteria is selected from the genus Lactobacillus.

4. A method as set forth in claim 3, wherein said bacteria is present in a non-toxic oil emulsion.

5. A method as set forth in claim 4, wherein each of said steps is repeated.

6. A method as set forth in claim 1, wherein said bacteria comprises *Lactobacillus acidophilus* and *Lactobacillus casei*.

7. A method as set forth in claim 1, wherein said bacteria is selected from the group consisting of *Lactobacillus acidophilus* and *Lactobacillus casei*.

8. A method as set forth in claim 1, wherein said introducing step comprises introducing an oil emulsion comprising both an oil soluble and water soluble ensulsifier.

9. A method as set forth in claim 8, wherein said emulsifiers, in admixture, comprises an HLB of from about 3 to 15.

10. A method as set forth in claim 8, wherein said oil emulsion comprises an unsaturated vegetable oil.

11. A method as set forth in claim 8, wherein the live bacteria count injected into said gland is within the range of approximately $1 \times 10^3$ to $1 \times 10^9$ CFU per cc of said emulsion.

12. A method as set forth in claim 1, wherein said introducing step comprises introducing approximately 6 to 15 cc of said bacteria having a live bacteria count of approximately $1 \times 10^3$ to $1 \times 10^9$ CFU per cc.

13. A method of controlling mastitis in mammals distinguished by the presence of an udder, said method comprising:
   (a) introducing into said udder through the teat canal a mastitis controlling non-toxic quantity of an oil emulsion of one or more non-pathogenic live lactic acid producing bacteria,
   said bacteria being present in sufficient quantity to lower the pH of the udder to at least about 5.0 to 6.5;
   (b) allowing said bacteria to remain in said udder in a viable state until milk present in the udder is clabbered;
   (c) milking said udder to remove the clabbered milk.

14. A method as set forth in claim 13, wherein said introducing step comprises introducing an oil emulsion of said bacteria, said emulsion comprising both oil soluble and water soluble emulsifiers, wherein the HLB of said emulsifiers, in admixture, is from about 3 to 15.

15. A method as set forth in claim 14, wherein said bacteria count is at least about $1 \times 10^3$ CFU per cc of said emulsion and said bacteria is selected from the group consisting of *Lactobacillus acidophilus* and *Lactobacillus casei*.

16. A method as set forth in claim 15, wherein said bacteria consists of *Lactobacillus acidophilus* and *Lactobacillus casei*.

17. A method as set forth in claim 16 wherein said emulsion comprises a suspension agent selected from the group consisting of glycerin, polyethylene glycol, polypropylene glycol and sorbitol.

18. A method as set forth in claim 17, wherein said oil comprises an unsaturated vegetable oil.

19. A method as set forth in claim 18, wherein said introducing step comprises introducing approximately 6 to 15 cc of said emulsion.

20. A method as set forth in claim 19 wherein steps (a) through (c) are repeated.

21. A method of controlling mastitis in bovines, said method comprising:
   (a) introducing into the udder through the teat canal approximately 6 to 15 cc of a non-toxic oil emulsion of live bacteria selected from the group consisting of *Lactobacillus acidophilus*, and *Lactobacillus casei*, said live bacteria count being at least about $1 \times 10^3$ CFU per cc of said emulsion;
   (b) allowing said bacteria to remain in said udder in a viable state for approximately 8 to 12 hours thereby resulting in clabbering of the milk in the udder; and
   (c) milking said udder to remove the clabbered milk.

22. A method as set forth in claim 21, wherein steps (a) through (c) are repeated.

23. A method as set forth in claim 22, wherein said oil emulsion comprises a suspension agent and an unsaturated vegetable oil.

24. A method as set forth in claim 23, wherein said oil emulsion comprises both oil and water soluble emulsifiers, said emulsifiers, in admixture, having an HLB of about 3 to 15.

25. A method as set forth in claim 24, wherein said bacteria count is within the range of approximately $1 \times 10^3$ to $1 \times 10^9$ CFU per cc of said emulsion.

* * * * *